United States Patent
Jones

(10) Patent No.: US 9,463,283 B2
(45) Date of Patent: Oct. 11, 2016

(54) DOSING MECHANISM FOR A DRUG DELIVER DEVICE

(75) Inventor: Christopher John Jones, Gloucestershire (GB)

(73) Assignee: SANOFI-AVENTIS DEUTSCHLAND GMBH, Frankfurt Am Main (DE)

( * ) Notice: Subject to any disclaimer, the term of this patent is extended or adjusted under 35 U.S.C. 154(b) by 1681 days.

(21) Appl. No.: 12/788,718

(22) Filed: May 27, 2010

(65) Prior Publication Data

US 2011/0004191 A1   Jan. 6, 2011

Related U.S. Application Data

(60) Provisional application No. 61/182,844, filed on Jun. 1, 2009.

(30) Foreign Application Priority Data

Jul. 10, 2009   (EP) .................................. 09009049

(51) Int. Cl.
*A61M 5/31*   (2006.01)
*A61M 5/315*   (2006.01)

(52) U.S. Cl.
CPC ....... *A61M 5/31538* (2013.01); *A61M 5/3155* (2013.01); *A61M 5/31535* (2013.01); *A61M 5/31536* (2013.01); *A61M 5/31541* (2013.01); *A61M 5/31545* (2013.01); *A61M 5/31548* (2013.01); *A61M 5/31551* (2013.01); *A61M 5/31553* (2013.01); *A61M 5/31555* (2013.01); *A61M 5/31595* (2013.01); *A61M 2005/3154* (2013.01)

(58) Field of Classification Search
CPC .................... A61M 5/31553; A61M 5/31555; A61M 5/3155; A61M 5/31548; A61M 5/31545; A61M 5/31595; A61M 5/31591; A61M 5/31538; A61M 5/31536; A61M 5/31551; A61M 5/31535; A61M 5/31541; A61M 2005/3154

See application file for complete search history.

(56) References Cited

U.S. PATENT DOCUMENTS 2,283,915 A * 5/1942 Cole ................. A61M 5/31551
                                                             222/158
3,302,462 A   2/1967   Pursell
5,423,752 A   6/1995   Haber et al.

(Continued)

FOREIGN PATENT DOCUMENTS

DE   93 01 334 U1   4/1993
DE   197 30 999 C1   12/1998

(Continued)

OTHER PUBLICATIONS

Machine Deisgn, Penton Media, vol. 65, No. 11 (1993) p. 36 "Standard Compression Springs Save Space".

*Primary Examiner* — Laura Bouchelle
*Assistant Examiner* — Ahn Bui
(74) *Attorney, Agent, or Firm* — McDonnell Boehnen Hulbert & Berghoff LLP

(57) ABSTRACT

A maximum settable dose feature is disclosed that is set by a user or health care professional one time that prevents future injections from exceeding the desired maximum dose. The feature includes a locking band initially in an unlocked configuration, which transforms to a locked configuration when activated after setting a desired maximum dose. The feature can include a trigger mechanism to transform the locking band to the locked configuration.

19 Claims, 2 Drawing Sheets

(56) References Cited

U.S. PATENT DOCUMENTS

| | | | |
|---|---|---|---|
| 5,514,097 A | 5/1996 | Knauer | |
| 5,584,815 A | 12/1996 | Pawelka et al. | |
| 5,591,136 A | 1/1997 | Gabriel | |
| 5,792,117 A | 8/1998 | Brown | |
| 5,820,602 A | 10/1998 | Kovelman et al. | |
| 6,090,080 A | 7/2000 | Jost et al. | |
| 6,936,032 B1 | 8/2005 | Bush, Jr. et al. | |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |
| 2004/0210199 A1 | 10/2004 | Atterbury et al. | |
| 2004/0236285 A1 | 11/2004 | Fisher et al. | |
| 2005/0131354 A1* | 6/2005 | Tachikawa | A61M 5/31555 604/187 |
| 2005/0137571 A1 | 6/2005 | Hommann | |
| 2006/0153693 A1 | 7/2006 | Fiechter et al. | |
| 2006/0258988 A1 | 11/2006 | Keitel et al. | |
| 2007/0021718 A1 | 1/2007 | Burren et al. | |
| 2008/0027397 A1 | 1/2008 | DeRuntz et al. | |
| 2008/0077095 A1 | 3/2008 | Kirchhofer | |
| 2008/0208123 A1 | 8/2008 | Hommann | |
| 2009/0227959 A1 | 9/2009 | Hirschel et al. | |
| 2009/0275916 A1* | 11/2009 | Harms et al. | 604/506 |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

DOSING MECHANISM FOR A DRUG DELIVER DEVICE

THE TECHNICAL FIELD OF THE INVENTION

The present invention relates to a system for locking in a maximum settable dose for a drug delivery device that prevents a user from subsequently setting a dose greater than the initially set maximum dose. The maximum settable dose feature can be activated or triggered by the user or a health care professional.

DESCRIPTION OF RELATED ART

A number of known drug delivery devices are intended for multi-dose applications where the user can dial or set a dose prior to injection. One such settable dose injection device is a pen-type drug delivery device where a user regularly injects themselves, sometimes more than once a day. This is increasingly common among patients having diabetes where self-treatment enables such patients to conduct effective management of their disease. These pen-type injectors typically use some form of cartridge capable of delivering multiple doses of a specific type of medicine, such as human growth hormone or insulin. For a number of end users of such devices (typically patients being prescribed medicines) several injectors are needed to dispense a number of different medicaments. For example, diabetic patients may need one injection device containing long lasting insulin and a second injector containing short acting insulin. Clearly, it is important for such patients not to confuse the dose setting needed for one medicine with the dose setting needed for a different medicine. Likewise, it is highly desirable to prevent a user from administering an over dose of a medicine as this could be fatal. This is especially true for elderly patients, particularly those who are visually impaired or suffering from dementia. As such, there exists a strong need to provide users of such devices with a simple and clear means to permanently set a maximum settable dose so that each subsequent injection will not exceed that preset dose. There is also a need to provide a user with a means to set the same dose for each injection by providing a secure stop that is readily apparent to the user when a dose is being set.

My invention solves the above-described problems by providing a maximum settable dose feature that can be used in multi-dose injection devices, where the patient or a health care professional can activate or set the maximum dose before the first injection is made. These and other advantages will become evident from the following more detailed description of the invention.

SUMMARY OF THE INVENTION

The maximum settable dose feature of my invention can be used on practically any drug delivery device that is designed to deliver multi-doses. A particularly preferred type of delivery device is a pen-type injector where a user can set a dose before each injection by causing a rotation or linear movement of a dose setting component. The specific design of the dose setting component is not critical to my invention provided that this component in some manner initially causes the locking band of my invention to move to a position within the device that represents an initial set dose or the desired maximum settable dose. Once the locking band reaches this position, then a reversal of the motion of the dose setting component (rotational or linear) will cause the locking band to transition from an unlocked configuration to a locked configuration. In one embodiment of my invention the maximum dose setting feature involves a combination of a dose setting component and a locking band, where the band has an unlocked configuration in rotational or linear engagement with the dose setting component and a locked configuration that provides a permanent stop for the dose setting component during subsequent dose setting. The locking band transitions from the unlocked to the locked configuration after a first dose is set when the motion of the dose setting component is reversed. In an alternate embodiment, the locking band transitions to the locked configuration when the user activates a trigger mechanism, such as set pin, button, pull cord, latch or equivalent triggering mechanism.

A preferred configuration of the locking band is a circular or oblong sleeve-like structure. Preferably, it is positioned over a stationary part of the device and can move linearly or rotationally with respect to that stationary part when the dose setting component is moved during the setting of a first dose. In the unlocked configuration, the band is in an expanded state so that it does not frictionally engage the stationary part of the device that it is positioned on. In the locked configuration the band is contracted so that it frictionally engages the stationary part and is prevented from moving with respect to the dose setting component. A variety of methods and designs are possible for ensuring that the locking band is initially in the unlocked configuration. A preferred design is where the locking band has a spring finger, a leading edge and a trailing edge. The spring finger biases the leading edge away from the inner body when the locking band is in the first unlocked configuration. The trailing edge of the locking band grips the inner body when the locking band is in the second locked configuration. Alternatively, the band can be biased in the expanded or unlocked configuration by a shim, spacer, blank, pin, or other like biasing part that is directly or indirectly connected to the trigger mechanism, such that, when the user activates the trigger mechanism the band transitions to the locked configuration. A preferred biasing part is a spacer or pin connected to a pull ring that the user pulls out of the device after the first or maximum dose is set.

Yet another embodiment of or invention is an irreversible locking mechanism for setting a maximum dose for a drug delivery device comprising, in combination, an inner body having a distal end, a proximal end and a helical grove positioned along its axis from the proximal end to the distal end and a rotatable number sleeve. A threaded collar is attached to the number sleeve that rotates with number sleeve about the helical grove of the inner body. A locking band is positioned on the inner body having a first unlocked configuration and a second locked configuration. The locking band transitions from the first to the second configuration after a first dose is set.

Our invention also covers a method for setting a maximum dose, preferably a permanent maximum settable dose, in a drug delivery device. The method comprises rotating or pulling a dose setting component to set a first initial dose, which will thereafter correspond to the maximum settable dose for all future injections. When the dose setting component is moved to set the first dose, the locking band, in its unlocked position, is also caused to move to a position corresponding to this first or maximum dose. Like the dose setting component, the band can be moved in a linear or rotational motion. Once the initial dose is set, the user stops the rotation or linear movement of the dose setting component and reverses the movement of the dose setting component to cause the locking band to transition from the unlocked to the locked configuration. Alternatively, the user can activate a trigger mechanism to transform the locking band to the locked configuration. The locking band now acts as a rotational or linear stop to prevent the user from setting a subsequent dose larger than the first initial dose set.

The term "drug delivery device" according to instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The term "engaged" according to instant invention shall particularly mean the interlocking of two or more components of the drive mechanism/drug delivery device, e.g. a spline, thread, or meshed teeth connection, preferably the interlocking of helical grooves or threads of components ("rotationally engaged" or "threadedly engaged"). The term "first end" according to instant invention shall mean the proximal end. The proximal end of the device or a component of the device shall mean the end, which is closest to the dispensing end of the device. The term "second end" according to instant invention shall mean the distal end. The distal end of the device or a component of the device shall mean the end, which is furthest away from the dispensing end of the device.

BRIEF DESCRIPTION OF THE DRAWINGS

Without any limitation, my invention will be explained in greater detail below in connection with preferred embodiments and with reference to the drawings in which.

DETAILED DESCRIPTION OF THE EMBODIMENTS

Figure 1:
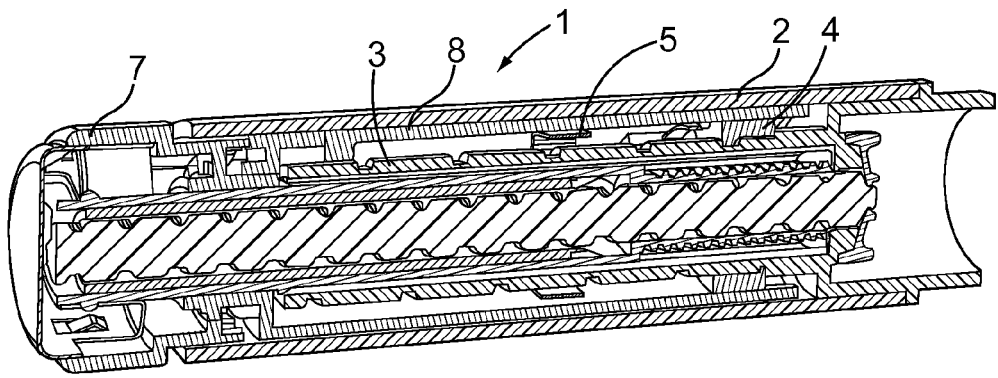
FIG. 1 shows a side sectional view of one embodiment of my invention where the locking band is positioned on a stationary part of the device.

Referring first to FIG. 1 there is shown a cross-sectional view of a dosing mechanism 1 for a pen-type injection device. As stated earlier, my maximum settable dose feature can be used with any number of multi-dose injection devices that allow a user to set a dose before each new injection. For illustrative purposes, the pen-type device shown in FIG. 1 has an outer housing 2 and an inner stationary body 3. The locking band 5 in this embodiment is shown as a tubular or ring shaped component position on stationary inner body 3 in an expanded unlocked configuration. In the unlocked configuration the locking band is rotationally engaged with threaded collar 4 that is threadedly engaged to stationary body 3.

The locking band may be fabricated from metal or any other durable material that is capable of gripping the stationary body when the locking band is in the contracted or locked configuration such that is acts as a rotational or linear stop during dose setting. For embodiments describe below, the locking band is illustrated as a metal pressing which grips the surface of a stationary body to produce a frictional interface between the relatively soft plastic material of the inner body and the relatively hard sharp edge of the metal locking band. This type of friction mechanism has the advantage of being settable in infinite rotational and angular positions. The geometry of the locking band could be such that the higher the force exerted upon it by the dose setting component, the higher the gripping force it exerts on the stationary member of the injection device. Alternatively, the locking band could be fabricated as a plastic molding with a spline or tooth feature that engages with corresponding features on the stationary member.

Figure 2:
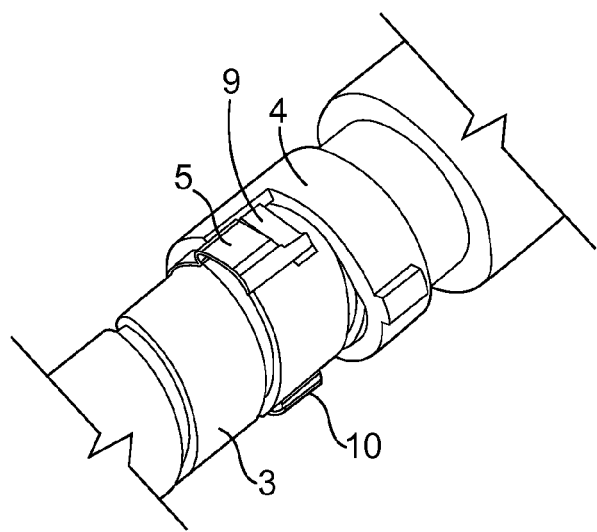
FIG. 2 shows a close up perspective view of the embodiment shown in FIG. 1.

Preferably, during assembly of the injection device, the maximum settable dose feature is assembled with the locking band expanded and free to move relative to the stationary body. This can be accomplished by using a spring finger to lift the leading edge of the locking band and hold it in the expanded state as shown in FIG. 2. For this embodiment the spring finger is a combined feature of the threaded collar. In the embodiment shown the trailing edge grips or at least is in contact with the inner body before the locking band is in its fully locked configuration. It is able to rotate around the inner body during the first dose setting because the self-locking geometry only works in the dial in direction. The threaded collar can be considered a dose setting component for the purposes of this embodiment, however, those skilled in the art will appreciate that number sleeve 8 or dose setting knob 7 could equivalently be referred to as a dose setting component. Indeed, by dose setting component I mean any component of the injection device that moves (linearly or rotationally) during the setting of a first dose and that causes (directly or indirectly) the locking band to move (linearly or rotationally) to a position corresponding to a desired maximum settable dose. In the embodiment shown in FIGS. 1 and 2 the threaded collar moves exactly with the number sleeve because it is fixed both axially and rotationally to the number sleeve.

Figure 3:
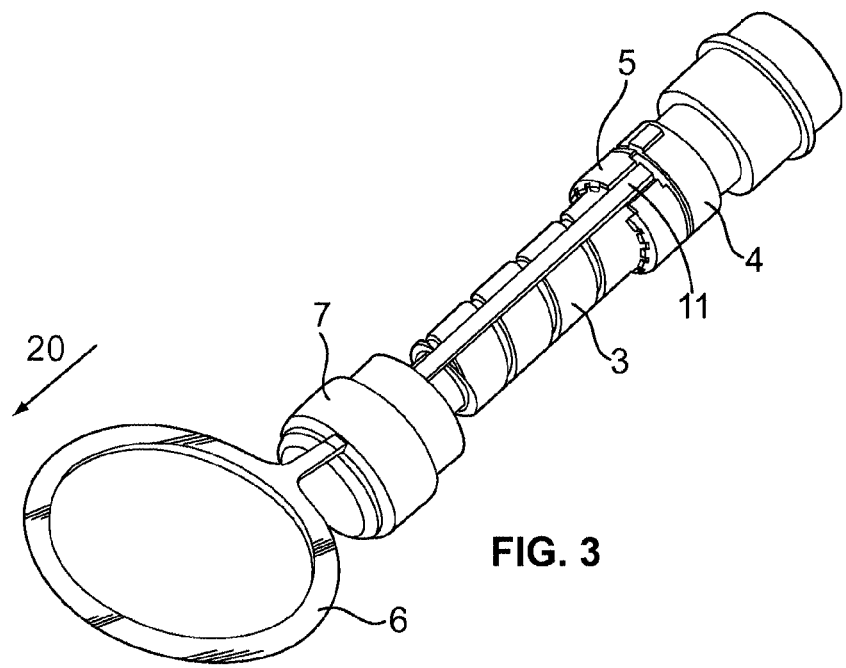
FIG. 3 shows a perspective view of another embodiment of my invention where a trigger is used to maintain the locking band in an unlocked configuration.

To set a dose, the user will turn dose setting knob 7, which in turn will rotate the number sleeve 8 that will turn threaded collar 4, which, because it is threadedly engaged to stationary body 3, will translate in the proximal direction (see direction arrow 20 in FIG. 3). As such, when a dose is being set, the threaded collar travels along the helix of the inner body carrying the locking band with it. Spring finger 9 holds the leading edge of the locking band away from the shank of the stationary inner body 3 preventing locking between the two components. When the desired dose size is reached the user pushes or rotates the dose setting component inwards. In the case of the embodiment shown in the Figures, the user rotates dose setting knob 7 in the opposite direction used to set the dose. In dialing down the direction of rotation of the threaded collar 4 combines with the self locking geometry of the trailing edge 10 of the locking band 5 causing the locking band 5 to grip or frictionally engage with the inner body 3 preventing the locking band from rotating and thus causing it to become separated from the threaded collar. When separated from the threaded collar the locking band contracts and irreversibly engages the inner body. The locking band is now in the locked configuration and acts a stop corresponding to the selected maximum settable dose. In this condition the locking band cannot rotate in either the inward or outward direction. Thus when the user sets subsequent doses the threaded collar will come into contact with the stationary locking band acting as a hard stop at a dose equal to the maximum dose set initially. The stationary locking band prevents the dose setting component, i.e. the threaded collar, the number sleeve or the dose setting knob, from rotating beyond the maximum dose position that it defines.

Figure 4:
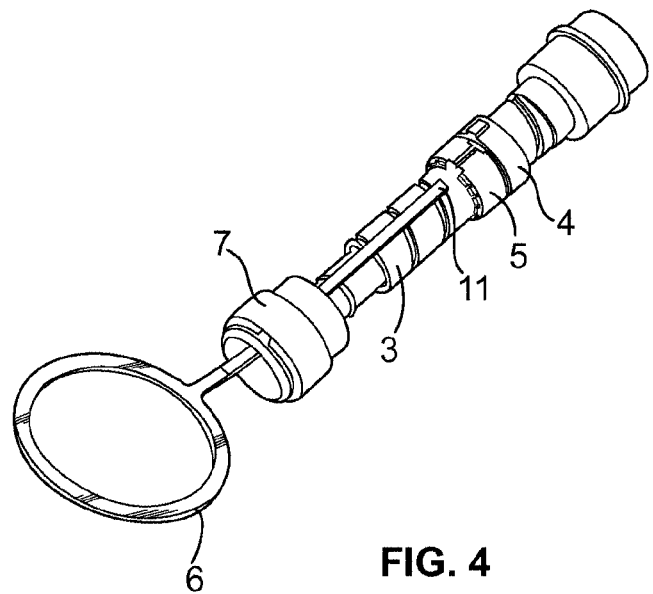
FIG. 4 shows a perspective view of the embodiment of FIG. 3 where the trigger has been activated and the locking band is in the locked configuration.

Referring now to FIG. 3 there is shown another embodiment of my maximum settable dose feature that can be used on any number of known multi-dose injection devices. For illustrative purposes, the same injection device design as shown in FIGS. 1 and 2 is presented. In this embodiment a trigger mechanism or setting pin shown as a combination pull ring 6 and biasing member 11. The locking band is held in its expanded condition by biasing member 11. With the setting pin in place the locking band is in its unlocked configuration where it is expanded and free to move relative to inner body 3 with dose setting component, i.e. the threaded collar, the number sleeve or the dose setting knob. Preferably, the injection device is assembled with the trigger in place. When the user dials the first dose with the setting pin in place, the locking band is free to move with the dose setting component to a position corresponding to the desired maximum settable dose for all future injections. Once this maximum settable dose is reached, the trigger is activated, or in the case of the embodiment shown in FIG. 3, it is pulled in the proximal direction 20 as shown in FIG. 4. This causes the biasing member to disengage the locking band, which causes it to contract and transform into the locked configuration similar to what was described above in reference to FIGS. 1 and 2. In this condition the locking band cannot rotate or move axially relative to the inner body. Thus when the device is next dialed outward the threaded collar/number sleeve contacts the locking band and is prevented from rotating beyond the maximum dose size position.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The means, materials, and steps for carrying out various disclosed functions may take a variety of alternative forms without departing from the invention. Thus, the expressions "means to . . . " and "means for . . . ", or any method step language as may be found in the specification above or the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation within the terms of the following claims.

The invention claimed is:

1. A maximum settable dose feature for a drug delivery device comprising, in combination,
   a) a movable dose setting component configured to move in a first direction and a reverse direction opposite the first direction to set a first dose;
   b) a locking band having an unlocked configuration in rotational or linear engagement with the dose setting component and a locked configuration that provides a permanent stop for the dose setting component;
   c) a collar engaged with the dose setting component such that the collar moves proximal with the dose setting component;
   wherein the locking band in the unlocked configuration is engaged with the collar such that it moves in a proximal direction during the setting of the first dose and is configured to transition from the unlocked to the locked configuration after a first dose is set and when the collar is disengaged from the locking member and moved in a distal direction, and
   wherein the locking band is further configured to transition from the unlocked configuration to the locked configuration when disengaged from the dose setting component as a result of the dose setting component being rotated or linearly moved in the reverse direction.

2. The maximum settable dose feature of claim 1 where the locking band has a greater diameter in the unlocked configuration than when in the locked configuration.

3. The locking mechanism of claim 1 where the locking band has a leading edge and a trailing edge and engages with a spring finger, wherein the spring finger holds one or both edges of the locking band in the unlocked configuration prior to setting of the first dose.

4. The locking mechanism of claim 1 further comprising a release trigger that maintains the locking band in the first unlocked configuration and wherein the locking band transitions from the first to the second position after a first dose is set when a user activates the trigger.

5. An irreversible locking mechanism for setting a maximum dose for a drug delivery device comprising, in combination,
   a) a stationary inner body having a distal end, a proximal end and a helical grove positioned along its axis from the proximal end to the distal end;
   b) a rotatable number sleeve;
   c) a threaded collar attached to the number sleeve that rotates and moves proximally with number sleeve about the helical grove of the inner body during setting of a first dose;
   d) a locking band having a first unlocked configuration on the inner body and being engaged with the collar such that it moves in a proximal direction during the setting of the first dose and having a second locked configuration on the inner body;
   wherein the locking band transitions from the first to the second configuration after a first dose is set as a result of the threaded collar being rotated in a reverse direction causing the collar to disengage from the locking band and to move in a distal direction, and
   wherein the locking band in the second locked configuration is rotationally fixed to the inner body through frictional engagement.

6. The locking mechanism of claim 5 where the locking band has a leading edge and a trailing edge and engages with a spring finger, wherein the spring finger holds one or both edges of the locking band in the unlocked configuration prior to setting of the first dose.

7. The locking mechanism of claim 6 where the spring finger biases the leading edge away from the inner body when the locking band is in the first unlocked configuration.

8. The locking mechanism of claim 6 where the trailing edge of the locking band grips the inner body when the locking band is in the second locked configuration.

9. The locking mechanism of claim 5 where the locking band is rotatably engaged by the threaded collar when the locking band is in the unlocked configuration and is free to rotate about the inner body.

10. The locking mechanism of claim 5 where the locking band is disengaged from the threaded collar after a first dose is set and is irreversibly locked to the inner body.

11. The locking mechanism of claim 5 wherein the locking band in the locked configuration is a dose stop defining a maximum settable dose that engages the threaded collar during setting of a second dose.

12. A method of setting a permanent maximum settable dose in a drug delivery device having,
   a) a movable dose setting component;
   b) a locking band having an unlocked configuration in rotational or linear engagement with the dose setting component and a locked configuration that provides a permanent stop for the dose setting component; wherein the locking band transitions from the unlocked to the locked configuration after a first dose is set; and
   c) a collar engaged with the dose setting component and the locking band such that collar and locking band move with the dose setting component during setting of the first dose;
   the method comprises,
   c) rotating or pulling the dose setting component to set a first dose;
   d) rotating or pulling the locking band in the unlocked position while in rotational or linear engagement with the dose setting component;
   e) stopping rotation or linear movement of the dose setting component when the first dose is reached; and
   f) reversing rotation or linear movement of the dose setting component causing the collar to disengage from the locking band to allow the locking band to transition from the unlocked to the locked configuration.

13. A method of setting a permanent maximum settable dose in a drug delivery device having,
   a) an inner body with a distal end, a proximal end, and a helical grove positioned along its axis from the proximal end to the distal end;
   b) a rotatable number sleeve;
   c) a threaded collar attached to the number sleeve that rotates with number sleeve about the helical grove of the inner body;
   d) a locking band having a first unlocked configuration on the inner body and a second locked configuration on the inner body; the method comprises,
   e) rotating the number sleeve to set a first dose;
   f) rotating the threaded collar with the number sleeve during setting of the first dose, where the threaded collar and number sleeve move in the proximal direction with the threaded collar engaging the helical grove of the inner body;
   g) rotating the locking band in the unlocked position while in rotational engagement with the threaded collar;
   h) stopping rotation of the number sleeve when the first dose is reached; and
   i) reversing rotation of the number sleeve causing the threaded collar to move distally along the helical grove of the inner body and to disengage from the locking band causing the locking band to irreversible engage the inner body.

14. The method of claim 13 where the locking band has a leading edge and a trailing edge and engages with a spring finger, and rotating the threaded sleeve in a distal direction causes the spring finger to release a biasing force on the leading edge and contracting the locking band to irreversibly engage the inner body.

15. An irreversible locking mechanism for setting a maximum dose for a drug delivery device comprising, in combination,
   a) a stationary inner body having a distal end, a proximal end, and a helical grove positioned along its axis from the proximal end to the distal end;
   b) a rotatable number sleeve;
   c) a threaded collar attached to the number sleeve that rotates with a number sleeve while engaged with the helical grove of the inner body, where the threaded collar is in rotational engagement with the number sleeve during setting of a first dose such that the threaded collar and number sleeve move in the proximal direction as the threaded collar is rotationally engaged with the helical grove of the inner body;
   d) a locking band having a first unlocked configuration on the inner body and a second locked configuration on the inner body, where the locking band when in the unlocked configuration is in rotational engagement with the threaded collar such that the locking band rotates;
   e) a release trigger that maintains the locking band in the first unlocked configuration; and
   wherein the locking band transitions from the first to the second configuration after a first dose is set when a user activates the trigger, and
   wherein the locking band in the second locked configuration is rotationally fixed to the inner body through frictional engagement.

16. The locking mechanism of claim 15 wherein the trigger comprises an elongated member having a distal end and a proximal end, where the distal end is in compression engagement with the locking band in the unlocked configuration and the proximal end is exposed to the user for grasping and activating the trigger.

17. The locking mechanism of claim 16 wherein the proximal end of the trigger comprises a pull ring for grasping by the user.

18. A method of setting a permanent maximum settable dose in a drug delivery device having,
   a) an inner body with a distal end, a proximal end, and a helical grove positioned along its axis from the proximal end to the distal end;
   b) a rotatable number sleeve;
   c) a threaded collar attached to the number sleeve that rotates with number sleeve about the helical grove of the inner body;
   d) a locking band having a first unlocked configuration on the inner body and a second locked configuration on the inner body;
   e) a release trigger that maintains the locking band in the first unlocked configuration; the method comprises,
   f) rotating the number sleeve to set a first dose;
   g) rotating the threaded collar with the number sleeve during setting of the first dose, where the threaded collar and number sleeve move in the proximal direction with the threaded collar engaging the helical grove of the inner body;

h) rotating the locking band in the unlocked position while in rotational engagement with the threaded collar;

i) stopping rotation of the number sleeve when the first dose is reached; and j) activating the trigger and causing the locking band to irreversible engage the inner body.

19. The method of claim 18 wherein a user pulls the trigger causing the locking band to transition from the unlocked to the locked configuration where it irreversibly engages the inner body.

\* \* \* \* \*